(12) United States Patent
Bindas

(10) Patent No.: US 7,867,179 B2
(45) Date of Patent: Jan. 11, 2011

(54) PROTECTIVE COVERING PROCESS

(76) Inventor: Jan J. Bindas, P.O. Box 691024, Orlando, FL (US) 32869-1024

( * ) Notice: Subject to any disclaimer, the term of this patent is extended or adjusted under 35 U.S.C. 154(b) by 1023 days.

(21) Appl. No.: 11/074,280

(22) Filed: Mar. 4, 2005

(65) Prior Publication Data

US 2006/0200056 A1 Sep. 7, 2006

(51) Int. Cl.
*A61F 5/00* (2006.01)
(52) U.S. Cl. .......................................... 602/3
(58) Field of Classification Search ............ 602/3, 602/20, 23, 79; 128/846, 849, 878, 882
See application file for complete search history.

(56) References Cited

U.S. PATENT DOCUMENTS

| | | | |
|---|---|---|---|
| 2,229,575 A | 1/1941 | Kaplan | |
| 2,334,206 A | 11/1943 | Knohl | |
| 3,324,580 A | 6/1967 | Baxter | |
| 3,741,203 A | 6/1973 | Liman | |
| 3,785,374 A | 1/1974 | Lipson | |
| 3,934,582 A * | 1/1976 | Gorrie ........................ | 602/62 |
| 3,957,048 A | 5/1976 | Jacobs | |
| 4,036,220 A | 7/1977 | Bellasalma | |
| 4,043,326 A | 8/1977 | Little et al. | |
| 4,098,268 A | 7/1978 | Scott | |
| 4,139,003 A | 2/1979 | Little et al. | |
| 4,224,935 A | 9/1980 | Metelnick | |
| 4,254,765 A | 3/1981 | Brown et al. | |
| 4,346,699 A | 8/1982 | Little et al. | |
| 4,363,317 A | 12/1982 | Broucek | |
| 4,423,722 A | 1/1984 | Dickman | |
| 4,523,586 A | 6/1985 | Couri | |
| 4,530,350 A | 7/1985 | Brown et al. | |
| 4,562,834 A * | 1/1986 | Bates et al. ................... | 602/3 |
| 4,610,245 A | 9/1986 | Biearman | |
| 4,646,727 A | 3/1987 | Chambers | |
| 4,727,864 A * | 3/1988 | Wiesenthal et al. ........... | 602/3 |
| 4,768,501 A | 9/1988 | George | |
| 4,911,151 A | 3/1990 | Rankin et al. | |
| 4,966,135 A | 10/1990 | Renfrew | |
| 4,986,265 A | 1/1991 | Caponi | |
| 5,016,622 A | 5/1991 | Norvell | |
| 5,063,919 A | 11/1991 | Silverberg | |
| 5,086,763 A | 2/1992 | Hathman | |
| 5,173,967 A * | 12/1992 | Carter ........................... | 2/242 |
| 5,187,813 A * | 2/1993 | Klein ........................... | 2/16 |
| 5,342,286 A | 8/1994 | Kelly et al. | |
| 5,395,302 A * | 3/1995 | Botha et al. .................. | 602/3 |
| 5,592,953 A | 1/1997 | Delao | |

(Continued)

*Primary Examiner*—Kim M Lewis
(74) *Attorney, Agent, or Firm*—William M. Hobby, III

(57) ABSTRACT

A process for applying a protective covering for a cast or wound to a patient includes the steps of selecting an elongated waterproof flexible transparent polymer bag having an opening in at least one end thereof and then cutting the selected bag to a predetermined length and sliding it over a patient's appendage to cover a cast or wound. A roll of elongated high cling plastic stretch film having a thickness between 50 and 200 gauge is then selected and wrapped around at least one end of the open end of the polymer bag adjacent the patient's appendage with a plurality of wraps while stretching the plastic stretch film to form a waterproof seal between the bag and the patient's appendage so that a waterproof cover is provided for the patient's wound or cast.

8 Claims, 2 Drawing Sheets

U.S. PATENT DOCUMENTS

| | | |
|---|---|---|
| 5,593,453 A | 1/1997 | Ahlert |
| 5,643,183 A | 7/1997 | Hill |
| 5,761,746 A * | 6/1998 | Brown .................. 2/243.1 |
| 5,817,038 A * | 10/1998 | Orange et al. ............ 602/3 |
| 6,047,403 A | 4/2000 | Juozaitis |
| 6,210,352 B1 * | 4/2001 | Williams et al. ........... 602/3 |
| D456,518 S * | 4/2002 | Ioannides ............. D24/190 |
| 2001/0041853 A1 | 11/2001 | South et al. |
| 2003/0154625 A1 | 8/2003 | Royle |

* cited by examiner

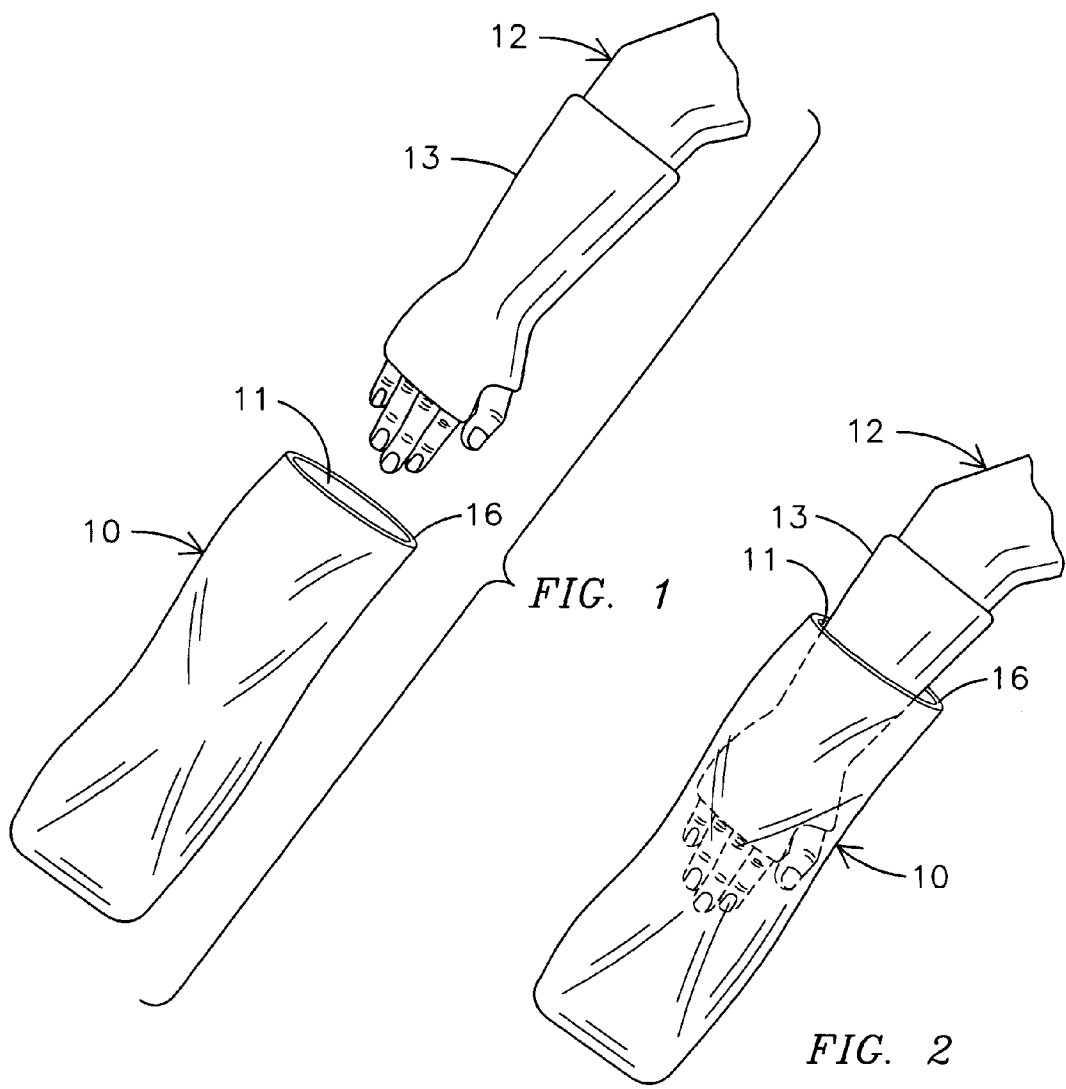
FIG. 1
FIG. 2
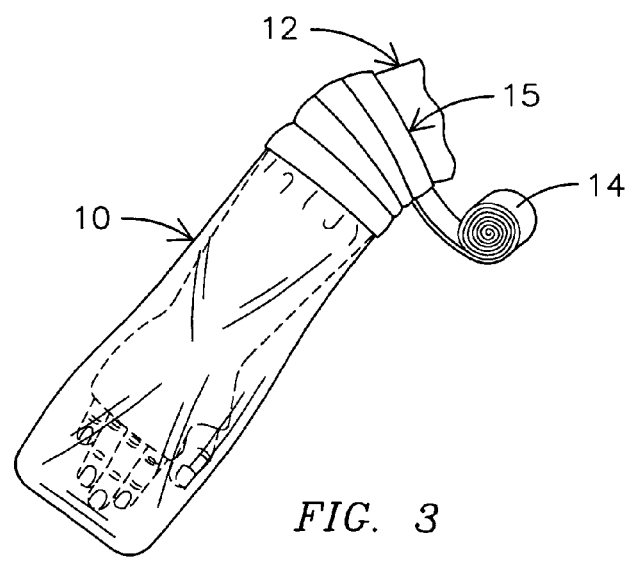
FIG. 3

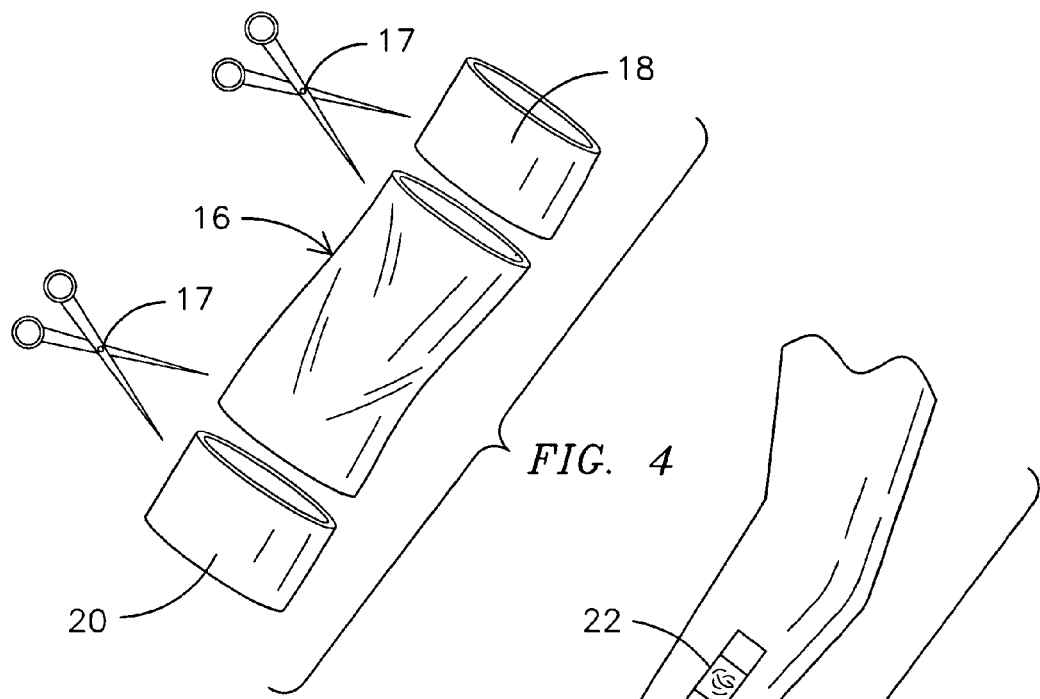
FIG. 4
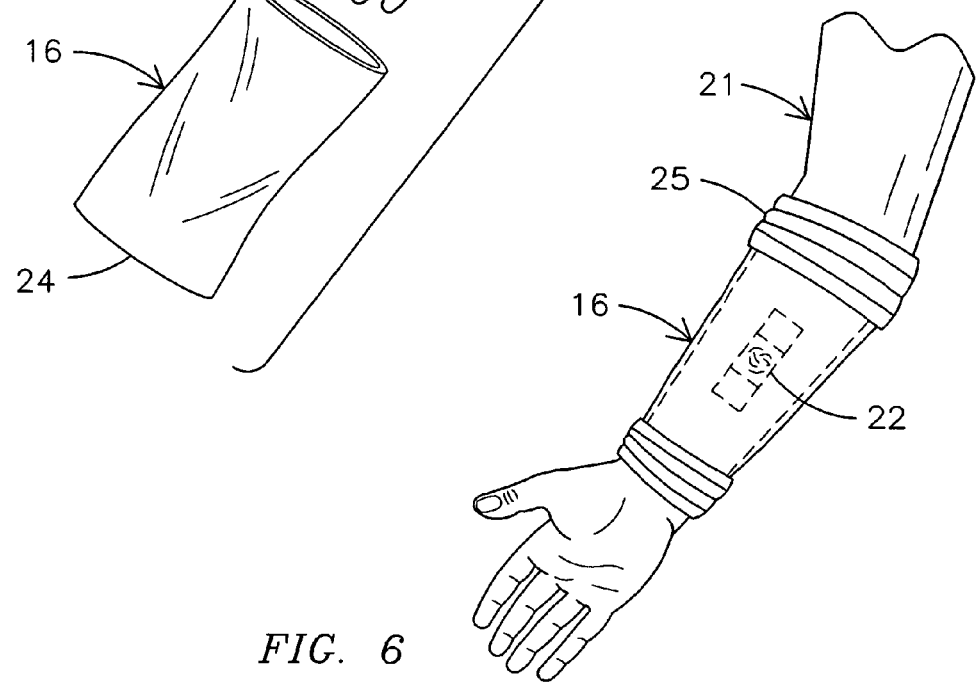
FIG. 5
FIG. 6

PROTECTIVE COVERING PROCESS

BACKGROUND OF THE INVENTION

The present invention relates to a process of applying a protective cover for covering a cast or a wound on a patient's appendage, such as an arm or leg, and especially to a process using a waterproof flexible transparent polymer bag to cover the cast or wound which is sealed with an elongated strip of high cling plastic stretch film.

It is well known that the plaster used to form a cast around broken or severely injured limbs and joints becomes soft and deteriorates when it gets wet. The patient is therefore required to make every effort to keep the cast dry at all times. In addition, a patient needs to make every effort to keep any kind of open wound on the patient's body dry at all times. A patient also needs to protect other types of casts from infiltration of water. A common practice with patients having casts is to cover the outside surface of the cast with a sheet of plastic in an attempt to prevent water from reaching the surface and inside of the cast. This arrangement requires a seal of some kind around the upper portion of the cast bound limb to prevent water from leaking between the limb and the covering piece of plastic. Homemade plastic seals of this type which provide for a seal tight enough to prevent water leakage also result in blocking the supply of blood to the injured limb and, if the seal is loose, water leakage may occur.

The present invention is directed towards a process for attaching a waterproof covering for a cast or body wound of a patient in which the cover is disposable and has a sealing arrangement which effectively prevents water from contacting the cast or wound and also does not stop the circulation of the blood to an injured limb.

There have been a large number of prior U.S. patents for covering a cast or sealing the cover for the cast to prevent the intrusion of water into the cast. Prior U.S. patents which use some type of wrapping or strap to a cast cover can be seen in the Caponi U.S. Pat. No. 4,986,265 for a protective cast cover which covers a cast with a protective plastic cover and wraps the end of the protective cover with a neoprene or foam plastic material to form the seal. In the Rankin et al. U.S. Pat. No. 4,911,151, a disposable dressing cover for an arm or a leg provides for a tubular plastic sleeve to fit over the cast and then has one end secured with a strap which is attached by an adhesive. In the Hill U.S. Pat. No. 5,643,183, a waterproof cover for a cast uses a transparent polyethylene bag and seals the distal ends with pairs of strips of hook and loop material. Similarly, the Bellasalma U.S. Pat. No. 4,036,220 has a protective cover and has a flexible collar to form the seal which is attached with hook and loop material. The Kaplan U.S. Pat. No. 2,229,575 has a flexible bag covering an artificial limb which is sealed with a sealing band. The Kelly et al. U.S. Pat. No. 5,342,286 provides a water impervious covering for extremities and uses an adhesive strip in the sealing of a flexible covering. The Broucek U.S. Pat. No. 4,363,317 is for a watertight cast cover for protecting a cast which is sealed with a band having overlapping ends forming flaps of hook and loop material. The U.S. patent to Biearman U.S. Pat. No. 4,610,245 is for a medical protective sleeve for a human limb which has a sealing cuff which is wrapped tightly around the limb. In the U.S. patent to Liman U.S. Pat. No. 3,741,203, a protective covering for an injured limb forms a seal with wrapping tape. In the Norvell U.S. Pat. No. 5,016,622 an immobilizing orthopedic cast is made of an inner water-impermeable protective sleeve next to the skin and a resilient padding layered with a plastic or resin or glass fiber outer immobilizing layer. In the Couri U.S. Pat. No. 4,523,586 a protective cover for a limb or cast is provided with a sealing band as is the Baxter U.S. Pat. No. 3,324,580. In the Delao U.S. Pat. No. 5,592,953, a wound cover is formed with a flexible sleeve sealed at each end.

In contrast to these and other prior patents, the present invention is for a disposable cast or wound cover which has a highly flexible covering bag which is sealed with an elongated piece of high cling plastic stretch film commonly used in the packing industry which is self-clinging to itself and which provides a seal to one end of the plastic covering when made with a plurality of overlapping wraps.

SUMMARY OF THE INVENTION

A process for applying a protective covering for a cast or wound to a patient includes the steps of selecting an elongated waterproof flexible transparent polymer bag having an opening in at least one end thereof and then cutting the selected bag to a predetermined length and sliding it over a patient's appendage to cover a cast or wound. A roll of elongated high cling plastic stretch film having a thickness between 50 and 200 gauge is then selected and wrapped around at least one end of the open end of the polymer bag adjacent the patient's appendage with a plurality of wraps while stretching the plastic stretch film to form a waterproof seal between the bag and the patient's appendage so that a waterproof cover is provided for the patient's wound or cast.

The high cling plastic stretch film may be from a polyethylene or from a PVC plastic and may be anywhere from one to six inches wide and it typically is stretchable between 10 and 30%. A selected polymer bag would typically have a thickness of greater than 1.5 mils. The process includes cutting the selected polymer bag at both ends and wrapping both ends with the elongated high cling plastic stretch film to seal both ends over a wound or cast.

BRIEF DESCRIPTION OF THE DRAWINGS

Other objects, features, and advantages of the present invention will be apparent from the written description and the drawings in which:

FIG. 1 is an exploded perspective view of a plastic bag being inserted over a patient's arm having a cast thereon;

FIG. 2 is a perspective view of the plastic bag being inserted over the patient's arm and cast;

FIG. 3 is a perspective view of the sealing of the plastic bag with high cling stretch tape;

FIG. 4 is an exploded perspective view of the plastic covering bag being cut from both ends;

FIG. 5 is an exploded perspective view of the cut bag of FIG. 4 being inserted over a patient's arm having a wound thereon; and FIG. 6 is a perspective view of a patient's arm wound covered with a plastic cover.

DETAILED DESCRIPTION OF THE PREFERRED EMBODIMENTS

Referring to the drawings, FIGS. 1-3, a process for applying a protective cover for a cast or wound to a patient is illustrated in which a disposable plastic bag 10 is an elongated, waterproof, flexible, and transparent plastic bag having an opening 11 in one end. The plastic bag may be a polyethylene or polypropylene polymer bag as desired and would typically be 1.5 mils or greater in thickness. In a typical kit for cast covers, the bag might be provided from several lengths, such as 8×24 inches; 10×30 inches; and 12×60 inches, which can then be cut to size. The bag is normally sealed at one end, as illustrated in FIGS. 1-3, and may be trimmed from the open end or may be trimmed from both ends as desired. The bag is advantageously larger than required to leave it loosely over a patient's arm 12 and cast 13, which is especially important in the case of a patient's wound being covered so that the plastic bag will not be tightly pressed onto a wound surface.

The selected bag 10 is being slid over the patient's arm 12 and cast 13 in FIG. 2 and is completely over the cast in FIG. 3. A roll of elongated high cling plastic stretch film 14 is selected having a thickness between 50 and 200 gauge. This stretch plastic film, which is commonly used in packing boxes and for other use, is typically polyethylene or polyvinyl chlorine or PVC that is used as wrapping material by stretching the film over a package load. Typically, the stretch film material is capable of stretching 10-30% while maintaining tension on the load elements. The thickness of the tape is usually expressed in "gauge" where 100 gauge equals 1/1000 of an inch and is typically provided in 60, 70, 80, 90, 120, and 135 gauges and comes in two, three and five inch widths. Thus, the tape is very thin and stretchable and self clinging to itself. The stretch film material is an elongated high cling plastic stretch film having a width of between 2 and 5 inches of high cling stretch film.

A roll of the high stretch film 14 is then wrapped at 15 in a plurality of overlapping wraps over the end 16 of the flexible polymer bag 10 using a plurality of wraps typically greater than four. Pulling the high cling stretch tape taunt to stretch the tape provides a complete seal while the tape is clinging to itself as it overlaps itself during wrapping. This high stretch film is inexpensive so as are the plastic bags 10 so that they are disposable after each use, as desired. A portion of a small adhesive strip or tab can be attached to the end of the high cling stretch tape prior to wrapping for holding to the bag when starting the wrap.

Turning to FIGS. 4-6, a second embodiment of the process of the invention is illustrated in which a selected elongated, waterproof, flexible, transparent plastic bag 16 has been cut to a desired length with a pair of scissors 17 at each end of the bag to remove portions 18 and 20 from the bag. The resized bag 16 is then slid over a patient's arm 21 which has a body wound 22 thereon so that the plastic bag 16 can cover the wound 22 when slid over the arm 21, as shown in FIG. 6. The bag 16 is then sealed at each end 23 and 24 with a plurality of wraps 25 made from a roll of elongated high cling plastic stretch film having a thickness between 50 and 200 gauge and which could typically be a film of 0.8 mils or about 23.3 microns. The film, as seen in FIG. 6, has a plurality of overlapping wraps so that the high cling film is both stretched taunt to provide a good seal and then clings to itself with each overlap, thus eliminating any other type of fastener and providing a disposable cast or wound cover.

It should be clear at this time that the process for applying a protective cover for a cast or wound to a patient has been provided which includes the steps of selecting an elongated waterproof flexible transparent polymer bag having an opening in at least one end thereof and then cutting the selected polymer bag to a predetermined length for covering a person's appendage and sliding the selected bag over a patient's appendage to cover a cast or wound. The process also includes selecting a roll of elongated high cling plastic stretch film having a thickness between 50 and 200 gauge and wrapping the elongated high cling stretch film around at least one end of the open end of a polymer bag adjacent the patient's appendage a plurality of times while stretching the elongated high cling stretch film taunt to form a waterproof seal between the bag and the patient's appendage so that a waterproof cover is provided for the patient's wound or cast. However, the present invention is not to be construed as limited to the forms shown which are to be considered illustrated rather than restrictive.

I claim:

1. A process for applying a protective covering for a cast or wound to a patient comprising the steps of:

selecting an elongated, waterproof, flexible, transparent polymer bag having an opening in at least one end thereof;

cutting said selected polymer bag to a predetermined length;

sliding said selected bag over a patient's appendage to cover a cast or wound;

selecting a roll of elongated high cling plastic stretch film having a thickness between 50 and 200 gauge and a width of between 2 and 5 inches; and wrapping said elongated high cling stretch film around at least one end of said open end of polymer bag adjacent said patient's appendage a plurality of times while stretching said elongated high cling stretch film to form a waterproof seal between said bag and the patient's appendage;

whereby a waterproof cover is provided for a patient's wound or cast.

2. The process for applying a protective covering for a cast or wound to a patient in accordance with claim 1 in which the step of selecting a roll of elongated high cling stretch film includes selecting a roll of polyethylene high cling stretch film.

3. The process for applying a protective covering for a cast or wound to a patient in accordance with claim 1 in which the step of selecting a roll of elongated high cling stretch film includes selecting a roll of polyvinyl chloride high cling stretch film.

4. The process for applying a protective covering for a cast or wound to a patient in accordance with claim 1 in which the step of selecting a roll of elongated high cling stretch film includes selecting a roll of high cling stretch film capable of stretching between 10 and 30 percent.

5. The process for applying a protective covering for a cast or wound to a patient in accordance with claim in which the step of selecting an elongated, waterproof, flexible, transparent polymer bag includes selecting an elongated, waterproof, flexible, transparent polymer bag having a thickness of greater than 1.5 mils.

6. The process for applying a protective covering for a cast or wound to a patient in accordance with claim 1 in which the step of selecting an elongated, waterproof, flexible, transparent polymer bag includes selecting an elongated, waterproof, flexible, transparent polymer bag having a thickness of about 1.5 mils.

7. The process for applying a protective covering for a cast or wound to a patient in accordance with claim in which the step of selecting an elongated, waterproof, flexible, transparent polymer bag includes selecting an elongated, waterproof, flexible, transparent polyethylene bag having a thickness of greater than 1.5 mils.

8. The process for applying a protective covering for a cast or wound to a patient in accordance with claim 1 in which the step of cutting said selected polymer bag to a predetermined length includes said selected polymer bag to form an opening at both ends thereof and wrapping said elongated high cling stretch film over both ends fo said polymer bag to form a waterproof seal between each end of said bag and said patient's appendage.

* * * * *